US00PP09162P

United States Patent [19]

Zaiger et al.

[11] Patent Number: Plant 9,162

[45] Date of Patent: Jun. 13, 1995

[54] PLUM TREE 'EMERALD BEAUT'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 338,950

[22] Filed: Nov. 14, 1994

[51] Int. Cl.[6] ..... A01H 5/00

[52] U.S. Cl. ..... Plt./38.1

[58] Field of Search ..... Plt. 38.1

*Primary Examiner*—James R. Feyrer

[57] ABSTRACT

A new and distinct variety of plum tree with the unique combination of the following desirable features:

1. Fruit with excellent flavor and eating quality.
2. Fruit that will remain firm on the tree three weeks after maturity (shipping ripe).
3. Fruit with a high degree of soluble solids (average 16.0 Brix).
4. Relatively uniform ripening of the fruit throughout the tree.
5. Heavy and regular production of fruit.
6. Fruit with good storage quality.
7. Vigorous upright growth.

1 Drawing Sheet

ORIGIN OF THE VARIETY

The present new and distinct variety of plum tree was originated by us in our experimental orchard located near Modesto, Calif., as a first generation seedling from a cross between Wickson plum (non-patented) and a selected seedling with the identification number 3W32LC. The pollen parent with the identification number 3W32LC originated as a selected seedling from seed of an open pollinated Red Beaut Plum (U.S. Plant Pat. No. 2,539). A large group of these first generation seedlings were planted and grown under careful observation by us and during which time we recognized the present variety to be a distinct and desirable tree and to have the fruit characteristics described above. We selected the variety for asexual reproduction and commercialization.

ASEXUAL REPRODUCTION OF THE VARIETY

The present variety of new plum tree was asexually reproduced by budding, as performed by us, in our experimental orchard located near Modesto, Calif., which shows that all characteristics of the tree and its fruit run true to the original form and are established and transmitted through succeeding propagations.

SUMMARY OF THE VARIETY

The present new and distinct variety of plum tree which is of large size, vigorous, upright in growth, and is a regular and productive bearer of large, clingstone fruit with excellent flavor and eating quality. The tree is further characterized by its novelty in producing fruit that is high in soluble solids (average Brix 16.0), is relatively uniform in ripening and will hold firm on the tree for three weeks after maturity (shipping ripe). In comparison to its female parent Wickson plum (non-patented), the tree blooms later in the spring, produces fruit that is sweeter (higher in soluble solids), has the ability to hold its fruit firm on the tree longer and is approximately one month later in maturity.

PHOTOGRAPHS OF THE VARIETY

The accompanying color photographs show typical specimens of the foliage and fruit of our new and distinct plum variety. The upper and lower surface of the leaves are being shown, as well as an exterior and sectional view of the fruit divided in the suture plane to reveal flesh coloration, pit cavity and a stone remaining in place. The photographs were taken shortly after the fruit was picked at maturity (firm ripe) and the colors are as nearly true as is reasonably possible in a color representation of this type.

DESCRIPTION OF THE VARIETY

The following is a detailed botanical description of the new distinct variety of plum tree, its flowers, foliage and fruit, as based on observations of specimens grown near Modesto, Calif., with color terminology (except those in common terms) in accordance with Reinhold Color Atlas by A. Kornerup and J. H. Wansher.

Tree:

*Size.*—Large.
*Vigor.*—Vigorous.
*Form.*—Upright.
*Density.*—Medium dense.
*Bearing.*—Regular.
*Productivity.*—Productive.

Trunk:

*Size.*—Medium to large.
*Texture.*—Medium shaggy.
*Color.*—Brown to coffee brown (5-E-5 to 5-E-7).

Branches:

*Size.*—Medium.
*Texture.*—Medium rough.
*Lenticels.*—Medium in number. Large size.
*Color.*—Brown to grayish brown.

Leaves:

*Size.*—Large. Average length — 5". Average width — 1½".
*Margin.*—Finely serrated.
*Form.*—Oblanceolate — pointed.
*Texture.*—Smooth.
*Glands.*—Globose. Size — small. Number varies from 0 to 4, Average number 2. Positioned on upper portion of petiole and on the base of the leaf blade, usually alternate.
*Color.*—Upper surface — green to dark green (29-F-4) to (29-F-6). Lower surface — grayish green to dull green (29-E-5) to (29-E-6).

Flower buds:
*Size.*—Medium.
*Length.*—Medium.
*Form.*—Plump.
Flowers:
*Size.*—Medium.
*Pollen.*—Present.
*Color.*—White.
*Blooming period.*—Mar. 1, 1993 to Mar. 7, 1993. Varies slightly with climatic conditions.
Fruit:
*Maturity when described.*—Firm ripe.
*Date of first picking.*—Aug. 2, 1993.
*Date of last picking.*—Aug. 8, 1993.
*Size.*—Large. Comparatively uniform. Average diameter axially — 2 7/16" to 2 9/16". Average transversely in suture plane — 2⅜" to 2½".
*Suture.*—Shallow — extends from base to apex.
*Ventral surface.*—Round — smooth.
*Form.*—Nearly globose, slightly elongated.
*Cavity.*—Rounded. Average length — ½". Average breadth — ½".
*Base.*—Slightly retuse.
*Apex.*—Usually pistol point, varies from rounded to pistol point.
*Stem.*—Medium length. Medium width.
Flesh:
*Texture.*—Firm.
*Juice.*—Moderate.
*Ripens.*—Evenly.
*Fibers.*—Small, tender.
*Flavor.*—Excellent, sweet, subacid.
*Eating quality.*—Excellent.
*Aroma.*—Very little.
*Color.*—Yellowish white near the stone to light yellow near skin surface (2-A-2) to (2-A-5). Pit cavity—varies from yellowish gray to grayish yellow (2-B-4) to (2-B-5).
Skin:
*Thickness.*—Medium.

*Texture.*—Medium — tenacious to flesh.
*Tendency to crack.*—None.
*Bloom.*—Moderate to heavy.
*Down.*—Wanting.
*Color.*—Light green to yellowish green (29-C-8) to (29-E-8).
Stone:
*Type.*—Clingstone.
*Size.*—Medium to large. Average length — 1 1/16". Average width — 11/16". Average thickness—7/16".
*Form.*—Ovate.
*Apex.*—Acute.
*Base.*—Straight to rounded.
*Sides.*—Nearly equal.
*Surface.*—Slightly pitted throughout.
*Tendency to split.*—None.
*Color.*—Tan to light brown — (5-B-5) to (5-D-7).
Use: Dessert. Market — Local and long distance.
Storage quality: Good.
Shipping quality: Fair to good.

The present new plum tree, its foliage, flowers and fruit herein described may vary in slight detail due to the climate, soil conditions and cultural practices under which the variety maybe grown. The present description is that of the variety grown under the ecological conditions prevailing near Modesto, Calif.

We claim:

1. A new and distinct variety of plum tree, substantially as illustrated and described, characterized by its large size, vigorous upright growth and being a regular and productive bearer of large, firm, clingstone fruit with excellent flavor and eating quality; the fruit is further characterized by relatively uniform maturity throughout the tree, holding firm on the tree for 3 weeks after maturity (shipping ripe) and, in comparison to its female parent Wickson plum (non-patented), it is approximately 30 days later in maturity.

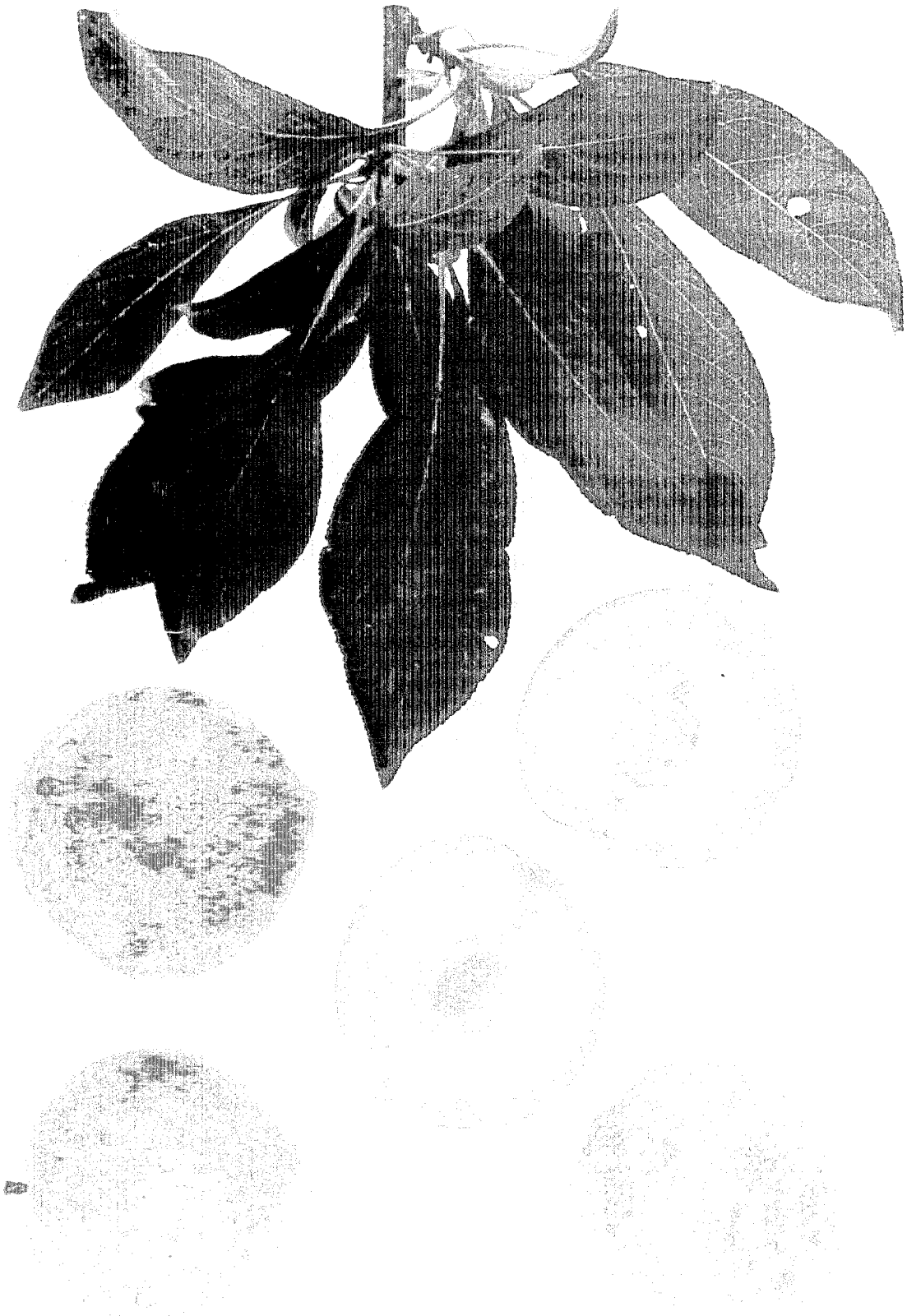

* * * * *